United States Patent [19]

Lamb et al.

[11] Patent Number: 5,530,187

[45] Date of Patent: Jun. 25, 1996

[54] TRANSGENIC PLANTS CONTAINING MULTIPLE DISEASE RESISTANCE GENES

[75] Inventors: Christopher J. Lamb; Qun Zhu, both of San Diego, Calif.; Eileen A. Maher, Madison, Wis.; Richard A. Dixon, Ardmore, Okla.

[73] Assignee: The Salk Institute for Biological Studies, La Jolla, Calif.

[21] Appl. No.: 93,372

[22] Filed: Jul. 16, 1993

[51] Int. Cl.[6] .............................. A01H 5/00; C12N 9/42; C12N 15/29; C12N 15/56; C12N 15/82

[52] U.S. Cl. .................... 800/205; 435/70.1; 435/172.3; 435/200; 435/209; 435/240.4; 435/320.1; 536/23.2; 536/23.6; 800/DIG. 43

[58] Field of Search ............................ 435/70.1, 172.3, 435/200, 240.4, 320.1, 209; 536/23.2, 23.6; 800/205, DIG. 25, 26, 42, 43, 44, 55, 56, 57, 58

[56] References Cited

U.S. PATENT DOCUMENTS

| | | | |
|---|---|---|---|
| 4,751,081 | 6/1988 | Suslow et al. | 424/93 |
| 4,940,840 | 7/1990 | Suslow et al. | 800/205 |
| 5,073,675 | 12/1991 | Jones et al. | 800/205 |
| 5,162,601 | 11/1992 | Slightom | 800/205 |
| 5,168,064 | 12/1992 | Bennett et al. | 435/320.1 |
| 5,173,419 | 12/1992 | Harman et al. | 435/209 |
| 5,177,308 | 1/1993 | Barton et al. | 800/205 |

FOREIGN PATENT DOCUMENTS 0440304  8/1991  European Pat. Off. ........ C12N 15/56

OTHER PUBLICATIONS

Broglie et al., "Transgenic Plants with Enhanced Resistance to the Fungal Pathogen *Rhizoctonia solani,*" *Science* 254:1194–1197 (1991).

Collinge, et al., "Plant chitinases," *The Plant Journal* 3:31–40 (1993).

Lamb et al., "Signals and Transduction Mechanisms for Activation of Plant Defenses against Microbial Attack," *Cell* 56:215–224 (1989).

Lamb et al., "Emerging Strategies for Enhancing Crop Resistance to Microbial Pathogens," *Bio/Technology* 10:1436–1445 (1992).

Mauch et al., "Antifungal Hydrolases in Pea Tissue," *Plant Physiol.* 88:936–942 (1988).

Neuhaus et al., "High–level expression of a tobacco chitinase gene in *Nicotiana sylvestris*. Susceptibility of transgenic plants to *Cercospora nicotianae* infection," 16:141–151 (1991) Plant Mol. Biol.

Boller, T. 1985. pp. 247–262 In: Cell. Mol. Biol. Plant Stress, Alan R. Liss, Inc.

Nishizawa et al. 1991. Plant Science 76:211–218.

Edington et al. 1991. Plant Mol. Biol. 16(1):81–94.

Shimamoto et al. 1989. Nature 338: 274–276.

Primary Examiner—David T. Fox
Attorney, Agent, or Firm—Pretty, Schroeder, Brueggemann & Clark; Stephen E. Reiter; Robert T. Ramos

[57] ABSTRACT

In accordance with the present invention, there are provided transgenic plants comprising a plurality of plant-defense-associated proteins that are expressed to produce such proteins in an amount sufficient to increase the plants resistance to plant pathogens, relative to non-transgenic plants of the same species. The transgenic plants are useful to study patterns of development, and to provide increased resistance to plant pathogens when grown in crops as a food source, and the like. Nucleic acid constructs are also provided that are useful in methods for producing the invention transgenic plants.

10 Claims, 3 Drawing Sheets

TRANSGENIC PLANTS CONTAINING MULTIPLE DISEASE RESISTANCE GENES

The present invention relates to transgenic plants containing at least two plant-defense-associated transgenes.

BACKGROUND OF THE INVENTION

The interactions between plants and various soil life forms are very complex, in some instances helpful to the plant and in other instances deleterious to the plant. Fungi harmful to plants (fungal pathogens) include fungal species from a wide variety of genera, including Fusarium, Pythium, Phytophthora, Verticillium, Rhizoctonia, Macrophomina, Thielaviopsis, Sclerotinia and numerous others. Plant diseases caused by fungi include pre- and post-emergence seedling damping-off, hypocotyl rots, root rots, crown rots, vascular wilts and a variety of other symptoms. Nematodes harmful to plants (nematode pathogens) include nematode species from the genera Meloidogyne, Heterodera, Ditylenchus, and Pratylenchus. Plant diseases caused by nematodes include root galls, root rot, lesions, "stubby" root, stunting, and various other rots and wilts associated with increased infection by pathogenic fungi. Some nematodes (e.g., Trichodorus, Lonoidorus, Xiphenema) can serve as vectors for virus diseases in a number of plants including Prunus, grape, tobacco and tomato.

Plant disease is the exception rather than the rule, as many plant pathogens express a virulent phenotype only on one or a limited number of host species. Pathogens inoculated onto a non-host species either lack the ability to grow and infect that plant, or following ingress invariably encounter a successful resistance mechanism. Interactions with host species exhibit a range of specificities dependent on the mechanism of the pathogen. One type of pathogen is the unspecialized "thug", which is necrotrophic and damages the host through production of toxins and/or enzymes. This pathogen is often equipped with inactivation or avoidance mechanisms to deal with host defenses. In contrast, "con men" pathogens grow biotrophically, avoiding serious host damage, at least in the early stages. Unlike thugs, con men pathogens do not activate host defenses nonspecifically.

For specialized pathogens having no avoidance mechanisms, host defenses are usually effective if induced. In specific interactions, following attempted infection by the pathogen, molecular signals determine whether the interaction will be incompatible or compatible. In an incompatible interaction (host resistant, pathogen avirulent), early molecular recognition is followed by rapid expression of defense responses. In a compatible interaction (host susceptible, pathogen virulent), the pathogen eludes the plant's surveillance mechanisms and disease generally ensues.

Various approaches have been utilized for attempting to control deleterious fungi and nematodes. One method is application of certain naturally occurring bacteria which inhibit or interfere with fungi or nematodes. See, for example, K. F. Baker and R. J. Cook, Biological Control of Plant Pathogens, Freeman and Co. (1974), for a description of fungi and nematodes and their interaction with plants, as well as a description of means for biological control of fungal and nematode pathogens. Another method is breeding for resistance, which is primarily focussed on the manipulation of minor resistance genes which make small quantitative contributions to the overall resistance of the plant.

Lytic enzymes have been individually transduced to form single-gene transgenic plants. For example, transfer of a tobacco basic vacuolar chitinase gene under the control of the CAMV35S promoter into the closely related species, N. sylvestris, did not give effective protection against C. nicotianae, even in transgenic plants exhibiting constitutively high levels of chitinase activity (Neuhaus et al., Plant Mol. Biol., 16:141–151, 1991). See also U.S. Pat. No. 4,940,840 to Suslow et al.

Recombinant bean chitinase has been expressed in transgenic tobacco seedlings (Broglie et al., *Science,* 254:1194–1197, 1991). The seedlings of the chitinase-containing transgenic plants have an enhanced, but not complete, resistance to a single species of fungi. Thus, it is desirable to obtain plants that have higher resistance levels to fungal pathogens than existing plants.

SUMMARY OF INVENTION

In accordance with the present invention, there are provided transgenic plants. Invention plants comprise a plurality of plant-defense-associated proteins that are expressed in an amount sufficient to increase the level of the plant's resistance to plant pathogens, relative to non-transgenic plants of the same species.

Plants or plant cells of the present invention are useful to study patterns of development, and to provide increased resistance to plant pathogens when grown in crops as a food source, and the like. Nucleic acid constructs are provided that are useful for producing the invention transgenic plants.

DETAILED DESCRIPTION OF THE INVENTION

Figure 1:
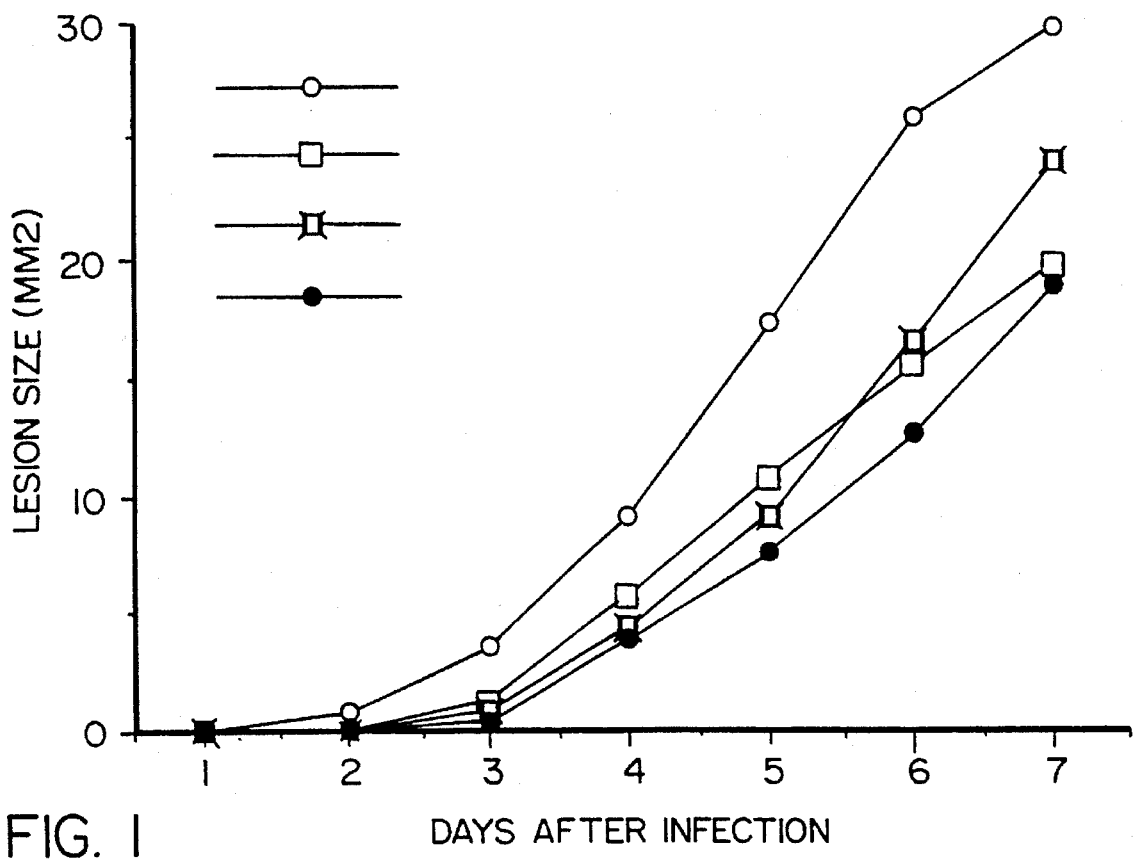
FIG. 1 shows the results of the *Cercospora nicotinae* fungal infection assay described in the Examples for the F4 generation invention transgenic tobacco plants. o=wild type tobacco plant, □=chitinase transgenic tobacco plant ■=glucanase transgenic tobacco plant, ●=chitinase/glucanase transgenic plant.

In accordance with the present invention, there are provided transgenic plants comprising:

a plurality of transgenes wherein each transgene encodes a plant-defense-associated protein.

In another embodiment, there are provided transgenic plants comprising:

a first transgene encoding a first overexpressed plant-defense-associated protein; and a second transgene encoding a second overexpressed plant-defense-associated protein, wherein the second plant-defense-associated protein is different from the first plant-defense-associated protein.

The term "plant" refers to whole plants, plant organs (e.g., leaves, stems, roots, etc.), seeds, plant cells, and the like. Plants contemplated for use in the practice of the present invention include both monocotyledons and dicotyledons. Exemplary monocotyledons contemplated for use in the practice of the present invention include rice, wheat, maize, sorgham, barley, oat, forage grains, as well as other grains. Exemplary dicotyledons include tomato, tobacco, potato, bean, soybean, and the like.

The phrase "plants of the same species" refers to plants that have substantially completely identical genotypes, except for the inheritable nucleic acid transgenes that are introduced by the methods disclosed herein.

A "transgenic plant" refers to a plant or plant material that contains an inheritable expression cassette containing a recombinant transgene. A transgenic plant according to the present invention is a plant or plant material that contains one or more inheritable recombinant nucleic acid expression cassettes encoding at least 2 total plant-defense-associated proteins. Preferably the invention transgenic plant contains at least 3 plant-defense-associated proteins, more preferably at least 5, with at least 10 plant-defense-associated proteins being most desirable.

The plant-defense-associated proteins may be encoded by a gene that is foreign to the recipient plant (with respect to species to which the recipient belongs, i.e., heterologous/exogenous), foreign only to the particular individual recipient (i.e., exogenous), or genetic information already possessed by the recipient (i.e., endogenous).

When an expression cassette contains an endogenous gene encoding a naturally occurring plant-defense-associated protein, the cDNA for such endogenous gene is operatively linked to a promoter different from its native promoter, such that the gene can be overexpressed relative to expression levels that naturally occur in the non-invention transgenic plant, i.e., the plant is capable of producing higher levels of the encoded protein than are naturally produced.

As used herein, an "overexpressed" plant-defense-associated protein refers to a protein that is produced in higher amounts than are produced endogenously. Overexpression can be achieved, for example, by linking a transgene to an appropriate constitutive promoter, such that the transgene is continually expressed. Alternatively, the transgene can be linked to a strong, inducible promoter so that overexpression can occur on demand.

Suitable levels of overexpression include expression of the transgene about 1.5-fold up to about 1000-fold or more over the naturally occurring level of expression of the endogenous transgene. Preferred levels of overexpression are at least about 5-fold, with at least about 10-fold over the naturally occurring level of expression of the endogenous transgene being especially preferred.

In a preferred embodiment of the invention, the transgenic plant comprises a first exogenous transgene encoding a first heterologous plant-defense-associated protein; and a second exogenous transgene encoding a second heterologous plant-defense-associated protein.

A "heterologous protein" refers to a plant-defense-associated-protein encoded by a transgene obtained from a species different from the species into which the heterologous protein is transduced (i.e., a species different from the invention transgenic plant species). Protein (or polypeptide) is a term used herein to designate a linear series of amino acid residues connected one to the other by way of a peptide bond. The heterologous protein may have distinctive properties relative to the properties of endogenously produced antimicrobial defense proteins. The heterologous protein is preferably constitutively expressed, although the natural expression of the endogenous gene encoding the protein may be inducible in response to stress.

Suitable "plant-defense-associated-proteins" contemplated for use in the invention transgenic plants are those classes of proteins that are involved in specific plant defense mechanism pathways, such as, for example, lytic enzymes, thaumatine-like proteins, α-thionin (e.g., Bohlmann et al., *EMBO J.*, 7:1559–1565, 1988), zeamatin (e.g., Vigers et al., *Mol. Plant Micro. Interactions*, 4:315–323, 1991) pathogenesis-related (PR) proteins (e.g., Bol et al., *Ann. Rev. Phytopathol.*, 28:113–138, 1990), ribosome-inactivating-proteins (RIPs) (e.g., Leach et al., *J. Biol. Chem.*, 266:1564–1573, 1990), lectins (e.g., Moreno et al., *PNAS, USA*, 86:7885–7889, 1989), cecropins, non-plant lysozymes, the *Bacillus thuringensis* toxin, enzymes involved in phytoalexin biosynthesis, proteinase inhibitors (e.g., Garcia-Olmedoz et al., *Surv. Plant Mol. Cell Biol.*, 4:275–334, 1987), inducers of plant disease resistance mechanisms, and the like.

As used herein, "lytic enzyme" refers to a protein that is able to enzymatically cleave a bond or bonds of a molecule that is essential for the survival of a known pathogen. Exemplary lytic enzymes include chitinase, glucanase, cellulase, trehalase, and the like. See also, Boller T., (1987) "Hydrolytic enzymes in plant disease resistance." in T. Kosuge, E. W. Nester, eds. Plant-Microbe Interactions. Vol 2. Macmillan, New York, pp 385–413, incorporated herein by reference in its entirety.

As used herein, "chitinase" refers to an enzyme that is capable of degrading chitin. In one embodiment, a chitinase construct that constitutively expresses the chitinase protein is employed. Preferably, the chitinase gene employed herein is rice basic chitinase. An exemplary sequence encoding rice chitinase is set forth in SEQ ID NO:1.

Other suitable chitinase genes for use herein are described, for example, in U.S. Pat. No. 4,940,840 to Suslow, incorporated herein by reference. See also the list of published chitinase nucleotide sequences in Table 1 of Collinge et al., *Plant Journal*, 3:31–40, (1993), incorporated herein by reference. In addition, suitable chitinase genes can be obtained employing methods well-known in the art. For example, the nucleic acid molecule of SEQ ID NO:1 can be used as a probe to isolate related genes with chitinase activity from genomic or cDNA libraries of organisms known to produce chitinase proteins, such as *Trichoderma harzianum*, strain P1 (ATCC No. 74058; see also U.S. Pat. No. 5,173,419). See Sambrook et al., *Molecular Cloning - - - A Laboratory Manual*, Cold Spring Harbor Laboratory. Cold Spring Harbor, N.Y., (1989).

In another embodiment, a glucanase construct that constitutively expresses the endo-1,4-β-glucanase protein is employed. The term "glucanase" refers to an enzyme that is capable of degrading callose. Preferably, the glucanase gene employed herein is a class II alfalfa acidic β-glucanase. An exemplary sequence encoding a class II alfalfa β-glucanase is set forth in SEQ ID NO:3.

Other glucanase genes (cDNA) suitable for use herein are derived from: tomato (ATCC No. 68312; see also U.S. Pat. No. 5,168,064, incorporated herein by reference), avocado (Christoffersen et al, *Plant Molec. Biol.*, 3:385, 1984) and bean (Tucker et al., *Plant Physiol.*, 88:1257, 1988). In addition, see the tobacco glucanase sequences described in: Payne et al., *Plant Mol. Biol.*, 15:797–808 (1990); Ward et al., *Plant Physiol.*, 96:390–397 (1991); and the glucanase sequence described in Linthorst et al., *PNAS,USA*, 87:8756–8760 (1990). Suitable glucanase genes can also be obtained employing methods well-known in the art. For example, the nucleic acid molecule of SEQ ID NO:3 can be used as a probe to isolate related genes with glucanase activity (see Sambrook et al., supra).

In a presently preferred embodiment of the present invention, the first and second proteins employed in the transgenic plant are chitinase and glucanase, respectively.

The plant-defense-associated proteins described herein are encoded by recombinant transgene molecules. As used herein, the term "transgene" refers to a DNA or RNA molecule. Transgenes employed herein encode a biologically active amino acid sequence (i.e., a protein). The term "plurality of transgenes" refers to greater than or equal to 2.total transgenes encoding plant-defense-associated proteins. Preferably the invention transgenic plant contains at least 3 different transgenes encoding plant-defense-associated proteins, more preferably at least 5, with at least 10 different transgenes being most desirable. One of skill in the art will recognize that the transgenes employed herein encode the necessary signals required for expression of a biologically active protein, such as appropriate leader peptide sequences and the like. A biologically active protein is a protein that has at least one of the physiological properties exhibited under naturally occurring physiological conditions.

The transgenes encoding the plant-defense-associated proteins are typically contained in expression cassettes. The phrase "expression cassette" refers to a DNA molecule that is able to direct the transcription and translation of a structural gene (i.e., cDNA) so that a desired protein is synthesized. The expression cassette comprises at least one promoter operatively linked to at least one transgene encoding a desired protein, and a transcription terminator sequence. Thus, the protein-encoding segment is transcribed under regulation of the promoter region, into a transcript capable of providing, upon translation, the desired protein. Appropriate reading frame positioning and orientation of the various segments of the expression cassette are within the knowledge of persons of ordinary skill in the art; further details are given in the Examples.

The promoter region refers to the portion of a gene that controls transcription of DNA to which it is operatively linked. The promoter region includes specific sequences of DNA that are sufficient for RNA polymerase recognition, binding and transcription initiation. The particular promoter selected should be capable of causing sufficient expression to result in the production of an effective amount of plant-defense-associated protein to increase the level of the plant's resistance to microbial infection. The amount of protein needed to induce resistance may vary with the type of plant. In a preferred embodiment, the promoter employed to express the transgenes is a constitutive promoter. It should be understood that this promoter may not be the optimal one for all embodiments of the present invention.

A "constitutive" promoter is a promoter which is active under all environmental conditions and all stages of development or cell differentiation. Constitutive promoters suitable for use in the practice of the present invention are widely available and are well known in the art. Exemplary constitutive promoters include the cauliflower mosaic virus 35S ("CaMV35S") promoter (see U.S. Pat. No. 5,097,925, incorporated herein by reference), CaMV19S promoter, nopaline synthase (NOS), octopine synthase (OCS), the rice actin gene promoter, and the like. In addition, the DNA promoter fragments from wheat described in U.S. Pat. No. 5,139,954; and plant promoters described in U.S. Pat. No. 5,097,025 are suitable for use herein. A presently preferred constitutive promoter for use in the practice of the present invention is CaMV35S.

The promoters used in the DNA constructs of the present invention may be modified, if desired, to affect their control characteristics. For purposes of this description, the phrase "CaMV35S" promoter thus includes variations of CaMV35S promoter, e.g., promoters derived by means of ligation with operator regions, random or controlled mutagenesis as well as, single, tandem or multiple copies of 35S enhancer elements, and the like.

In accordance with another embodiment of the present invention, there are provided nucleic acid construct(s) comprising the above-described expression cassette(s). The term "nucleic acid construct," or the abbreviated form "construct," as used herein, and throughout the specification and claims, refers to a recombinant nucleic acid molecule which can include expression cassettes, origins of DNA replication, procaryotic and eucaryotic genes from various sources (such as selectable marker genes), repressor genes, as well as any other sequence of nucleotides. The construct may be linear or in the circular form of a plasmid vector.

The nucleic acid construct of the present invention, including the segments of the expression cassette(s), are said to be "operably associated" with one another, such that said transgenes can be translationally expressed to produce the encoded protein under suitable conditions well-known to those of skill in the art.

As used herein the term "plasmid" or "vector" refers to circular, double-stranded DNA loops, which are not bound to the chromosome. One of skill in the art will recognize that the terms plasmid and vector can be used interchangeably. A plasmid contains DNA capable of causing expression of DNA sequences contained therein, where such sequences are in operational association with other sequences capable of effecting their expression, such as promoter sequences, and the like. The type and number of vectors employed is not critical, so long as greater than or equal to 2 transgenes are inheritable, e.g., capable of being expressed by each generation of plant. Suitable vectors for use in expressing the plant-defense-associated transgenes described herein include: pAMVBTS (ATCC No. 53637; Barton et al., *Plant Physiol.*, 85:1103–1109 (1987); pBI101 (Jefferson et al., *EMBO J.*, 6:3902–3907, 1987); and the pGEM and pSP vectors (Promega, Madison, Wis.). Presently preferred vectors for producing invention transgenic plants are the plasmids pBZ56, pM42X, and pBZ100, described hereinafter in the Examples section.

In accordance with yet another embodiment of the present invention, there are provided plant cells transformed with the above-described DNA construct(s).

The term "resistance," when used in the context of comparing the level of resistance between an invention transgenic plant and another plant, refers to the ability of the invention transgenic plant to maintain a desirable phenotype in the face of attack, relative to a non-transgenic plant or a single-gene transgenic plant. The level of resistance can be determined by comparing the physical characteristics of the invention plant to non-transgenic plants that either have or have not been exposed to microbial infection. Exemplary physical characteristics to observe include plant height, an increase in population of plants that have ability to survive microbial challenge (i.e., plants that come in contact with a compatible pathogen), delayed lesion development, reduced lesion size, and the like.

As used herein, "increased resistance to pathogens" refers to a level of resistance that an invention transgenic plant has to plant pathogens above a defined reference level. The defined reference level of resistance to a pathogen is the level of resistance displayed by non-transgenic or non-invention transgenic plants of the same species. Thus, the increased resistance is measured relative to previously existing plants of the same species. In one embodiment of the invention, the resistance is substantially increased above the defined reference level, e.g., greater than or equal to 20% above, preferably 50% above, more preferably 75% above; with up to 100% above being especially preferred.

The phrase "non-transgenic plants of the same species" means plants of the same species that do not contain any heterologous transgenes. The respective levels of pathogen resistance can be determined using well known methods including the Fungal Infection assays described hereinafter in the Examples section.

The phrase "transgenic plants of the same species that only express one exogenous transgene" refers to transgenic plants of the same species that only contain one transgene. These single-gene transgenic plants can contain any transgene including any one of the plurality of plant-defense-associated transgenes employed in the invention transgenic plant. Exemplary transgenic plants containing a single heterologous transgene include: glyphosate-resistant plants described in U.S. Pat. No. 5,188,642; and the plants described in Broglie et al., *Science*, 254:1194–1197 (1991); and Carmora et al., *Plant J.*, 3:457–462 (1992).

In one embodiment of the present invention, the level of resistance imparted by the invention construct is "synergistic." Synergistic resistance refers to a level of resistance provided by at least two plant-defense-associated proteins in a single transgenic plant that is greater than the combined resistance observed for each protein contained individually in at least two single-gene transgenic plants.

Methods of introducing the constructs employed herein into suitable host cells, as well as methods applicable for culturing said cells containing a gene encoding a heterologous protein, are generally known in the art. According to the invention, the vector is introduced into the host cell by any suitable means, e.g., transformation employing plasmids, viral, or bacterial phage vectors, transfection, electroporation, lipofection, and the like. The heterologous DNA can optionally include sequences which allow for the extrachromosomal maintenance of the expression cassette, or said expression cassette construct can be caused to integrate into the genome of the host (as an alternative means to ensure stable maintenance in the host). See, for example: the Agrobacterium mediated transformation of germinating plant seeds described in U.S. Pat. No. 5,169,770; the plant potyvirus expression vector described in U.S. Pat. No. 5,162,601; U.S. Pat. No. 5,168,064, each of which are expressly incorporated herein by reference.

In addition, cauliflower mosaic virus (CaMV) may be used as a vector for introducing nucleic acid constructs into plant cells. (Hohn et al., "*Molecular Biology of Plant Tumors,*" Academic Press, New York, pp. 549–560 (1982); Howell, U.S. Pat. No. 4,407,956). In accordance with the described method, the entire CaMV viral DNA genome is inserted into a parent bacterial plasmid creating a recombinant DNA molecule which can be propagated in bacteria. After cloning, the recombinant plasmid is further modified by introduction of the desired sequence into unique restriction sites in the viral portion of the plasmid. The modified viral portion of the recombinant plasmid is then excised from the parent bacterial plasmid, and used to inoculate the plant cells or plants.

Another suitable method of introducing DNA into plant cells is to infect a plant cell with *Agrobacterium tumefaciens* or *A. rhizogenes* that has previously been transformed with the gene. Under appropriate conditions known in the art, the transformed plant cells are grown to form shoots or roots, and develop further into plants. *Agrobacterium* is a representative genus of the gram-negative family Rhizobiaceae. Its species are responsible for crown gall (*A. tumefaciens*) and hairy root disease (*A. rhizogenes*). The plant cells in crown gall tumors and hairy roots are induced to produce amino acid derivatives known as opines, which are catabolized only by the bacteria. The bacterial genes responsible for expression of opines are a convenient source of control elements for chimeric expression cassettes. In addition, assaying for the presence of opines can be used to identify transformed tissue.

Heterologous genetic sequences can be introduced into appropriate plant cells, for example, by means of the Ti plasmid of *A. tumefaciens* or the Ri plasmid of *A. rhizogenes*. The Ti or Ri plasmid is transmitted to plant cells on infection by Agrobacterium and is stably integrated into the plant genome. J. Schell, *Science*, 237:1176–1183 (1987).

Ti and Ri plasmids contain two regions essential for the production of transformed cells. One of these, named transferred DNA (T-DNA), is transferred to plant nuclei and induces tumor or root formation. The other, termed the virulence (vir) region, is essential for the transfer of the T-DNA but is not itself transferred. The T-DNA will be transferred into a plant cell even if the vir region is on a different plasmid. Hoekema, et al., *Nature*, 303:179–189 (1983). The transferred DNA region can be increased in size by the insertion of heterologous DNA without affecting its ability to be transferred. A modified Ti or Ri plasmid, in which the disease-causing genes have been deleted, can be used as a vector for the transfer of the gene constructs of this invention into an appropriate plant cell.

Construction of recombinant Ti and Ri plasmids in general follows methods typically used with the more common bacterial vectors, such as pBR322. Additional use can be made of accessory genetic elements sometimes found with the native plasmids and sometimes constructed from foreign sequences. These may include but are not limited to "shuttle vector," [Ruvkun and Ausubel, *Nature*, 298:85–88 (1981)], promoters, [Lawton et al., *Plant Mol. Biol.*, 9:315–324 (1987)] and structural genes for antibiotic resistance as a selection factor [Fraley et al., *Proc. Nat. Acad. Sci.*, 80:4803–4807 (1983)].

There are two common ways to transform plant cells with *Agrobacterium:*

(1) co-cultivation of *Agrobacterium* with cultured isolated protoplasts (which requires an established culture system that allows for culturing protoplasts and subsequent plant regeneration from cultured protoplasts), or (2) transformation of intact cells or tissues with Agrobacterium (which requires that the intact plant tissues, such as cotyledons, can be transformed by Agrobacterium, and that the transformed cells or tissues can be induced to regenerate into whole plants).

Most dicot species can be transformed by Agrobacterium. All species which are a natural plant host for Agrobacterium are transformable in vitro. Monocotyledonous plants, and in particular, cereals, are not natural hosts to Agrobacterium. Attempts to transform them using Agrobacterium have been unsuccessful until recently. Hooykas-Van Slogteren et al., Nature, 311:763–764 (1984). There is growing evidence now that certain monocots can be transformed by Agrobacterium. Indeed, cereal species such as rye (de la Pena et al., Nature, 325:274–275 (1987), corn (Rhodes et al., Science 240:204–207 (1988), and rice (Shimamoto et al., Nature, 338:274–276 (1989) may now be transformed.

In one embodiment of the present invention, two expression cassettes containing transgenes encoding chitinase and glucanase are prepared as described above. The expression cassettes are combined into a single expression vector, to form a DNA construct which comprises two individual genes encoding plant-defense-associated proteins. The vector is then inserted into cultured A. tumefaciens cells which contain a disarmed Ti plasmid. In another embodiment of the present invention, two vectors are employed containing one expression cassette each. The two vectors are either transformed into a single plant or into separate plants.

Two separate transgenic plants that each contain expression cassettes having at least one transgene can be sexually crossed using well-known methods to produce a transgenic plant of the present invention. Any of a number of standard breeding techniques can be used, depending upon the species to be crossed.

In addition to plant transformation vectors derived from the Ti or root-inducing (Ri) plasmids of Agrobacterium, alternative methods can be used to insert the DNA constructs of this invention into plant cells. Such methods may involve, for example, the use of liposomes, electroporation, chemicals that increase free DNA uptake, and transformation using viruses. For example, the construct described above can be microinjected directly into plant cells by use of micropipettes to mechanically transfer the recombinant DNA. Crossway, Mol. Gen. Genetics, 202:179–185 (1985). The genetic material may also be transferred into the plant cell using polyethylene glycol, Krens, et al., Nature, 296:72–74 (1982).

Another method of introduction of transgene segments is high velocity ballistic penetration by small particles with the nucleic acid either within the matrix of small beads or particles, or on the surface (see, for example, Klein, et al., Nature, 327:70–73, 1987). Yet another method of introduction is fusion of protoplasts with other entities, either minicells, cells, lysosomes or other fusible lipid-surfaced bodies (see, for example, Fraley, et al., Proc. Natl. Acad. Sci. USA, 79:1859–1863, 1982).

The DNA may also be introduced into the plant cells by electroporation. Fromm et al., Pro. Natl. Acad. Sci. USA, 82:5824 (1985). In this technique, plant protoplasts are electroporated in the presence of plasmids containing the expression cassette. Electrical impulses of high field strength reversibly permeabilize biomembranes allowing the introduction of the plasmids. Electroporated plant protoplasts reform the cell wall, divide, and regenerate.

After transformation, transformed plant cells or plants comprising the invention nucleic acid constructs can be identified employing well-known methods. For example, a selectable marker, such as those discussed above, is typically used. Transformed plant cells can be selected by growing the cells on growth medium containing an appropriate antibiotic. The presence of opines can also be used if the plants are transformed with Agrobacterium.

After selecting the transformed cells, one can confirm expression of the desired heterologous gene. Simple detection of mRNA encoded by the inserted DNA can be achieved by well known methods in the art, such as Northern blot hybridization. The inserted sequence can be identified by Southern blot hybridization, as well.

Once the presence of the desired transgenes is confirmed, whole plant regeneration is desired. All plants from which protoplasts can be isolated and cultured to give whole regenerated plants can be transformed by the present invention. Some suitable plants include, for example, species from the genera Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Cichorium, Helianthus, Lactuca, Bromus, Asparagus, Antirrhinum, Hererocallis, Nemesia, Pelargonium, Panicum, Pennisetum, Ranunculus, Senecio, Salpiglossis, Cucumis, Browaalia, Glycine, Lolium, Zea, Triticum, Sorghum, Malus, Apium, Datura, and the like.

Plant regeneration from cultured protoplasts is described in Evans et al., Handbook of Plant Cell Cultures, Vol. 1: (MacMillan Publishing Co. New York, 1983); and Vasil, I.R. (ed.), Cell Culture and Somatic Cell Genetics of Plants, Acad. Press, Orlando, Vol. I, 1984, and Vol. III, 1986.

It is known that practically all plants can be regenerated from cultured cells or tissues, including but not limited to, all major species of sugarcane, sugar beet, cotton, fruit trees, and legumes.

Means for regeneration vary from species to species, but generally a suspension of transformed protoplasts or a petri plate containing transformed explants is first provided. Callus tissue is formed and shoots may be induced from callus and subsequently rooted. Alternatively, embryo formation can be induced employing well-known plant hormones in the callus tissue. These embryos germinate as natural embryos to form plants. The culture media will generally contain various amino acids and hormones, such as auxin and cytokinins. It is also advantageous to add glutamic acid and proline to the medium, especially for such species as corn and alfalfa. Efficient regeneration will depend on the medium, on the genotype, and on the history of the culture. If these three variables are controlled, then regeneration is usually reproducible and repeatable.

With the methods of the present invention, one can generate a transgenic plant containing at least a plurality of plant-defense-associated proteins, an origin of replication from either yeast, insect or mammalian cells, and a selectable marker gene for the expression of the plant-defense-associated proteins described herein.

The invention will now be described in greater detail by reference to the following non-limiting examples.

EXAMPLES

The nomenclature used hereafter and the laboratory procedures in recombinant DNA technology described below are those well known and commonly employed in the art. Standard techniques are used for cloning, DNA and RNA isolation, amplification and purification. Enzymatic reactions involving DNA ligase, DNA polymerase, restriction endonucleases and the like are performed according to the manufacturer's specifications. These techniques and various other techniques are generally performed according to Sambrook et al., *Molecular Cloning - - - A Laboratory Manual*, Cold Spring Harbor Laboratory. Cold Spring Harbor, N.Y., (1989). The manual is hereinafter referred to as "Sambrook." Other general references are provided throughout this document. The procedures therein are well known in the art and are described herein for the convenience of the reader. All the information contained therein is incorporated herein by reference.

Vector Preparation

Construction of plasmid pBZ56

A SphI fragment of rice chitinase RCH10 gene (SEQ ID NO: 1) from plasmid pRCH10 (described in Zhu et al., *Plant J.*, 3:203–212, 1993) was subcloned into pSP72 (Promega, Madison, Wis.) to give pBZ5B. A Sac2/KpnI fragment of RCH10 was subcloned into pSP72 to give pBZ52. The NcoI/EcoRV fragment of pBZ52 was inserted into pBZ5B NcoI/PvuII sites to give pBZ54. The EcoRV/BglII fragment of pBZ54 was inserted into pGEM721 BamHI/EcoRV sites to give pBZ55 [pGEM721 is a pGEM7 (Promega, Madison, Wis.) plasmid containing CaMV 35S promoter]. The HpaI/SacI fragment of pBZ55 was inserted into pBI101.1 (Jefferson et al., EMBO J., 6:3902–3907, 1987) to give pBZ56.

Construction of pM42X

A lambda ZAPII (Stratagene, La Jolla, Calif.) cDNA library prepared from poly (A) RNA isolated from alfalfa suspension cells 2, 3, and 4 h after elicitation with a fungal cell wall preparation (Dalkin et al., *Physiol. and Mol. Plant Path.*, 37:293–307, 1990) was screened using a bean glucanase cDNA as probe (Edington et al., *Plant Mol. Biol.*, 16:81–94, 1991). Positive plaques identified on duplicate filters were purified through two subsequent rounds of screening. Plasmids were then rescued in pBluescript SK- by use of the helper phage R408 (Stratagene), and insert size and diversity determined by restriction mapping. The largest insert that hybridized to the bean glucanase probe was subcloned into pGEM-3Zf(+) (Promega) to yield the plasmid "pAglu1", which contains the entire coding region for an isoform of acidic alfalfa $\beta$-1,3-glucanase (SEQ ID NO: 3).

A BamHI/XhoI fragment of pAglu1 containing an alfalfa $\beta$-glucanase gene was inserted into pMON530 (Monsanto, St. Louis, Mo.) BglII/XhoI sites to give pM4. The BamHI complete/PstI partial digested fragment of pM4 was inserted into pSP72 (Promega) to give pM42. The PvuII/SacI fragment of pM42 fragment was inserted into the SmaI/SacI site of pBI121 (Jefferson et al., *EMBO J.*, 6:3902–3907, 1987) to give pM42X.

Construction of pBZ100

The plasmid pBZ55, described above, was digested with EcoRV/SalI, filled in with DNA polymerase Klenow fragment and religated to give pBZ55M. An HpaI/XhoI fragment of pBZ55M was inserted into pGEM7 (Promega) to give pBZ55M-7. A SacI fragment of pBZ55M-7 was inserted into pM42X to give pBZ100.

Tobacco Transformation

Plasmids pBZ56 and pM42X were directly transformed in *Agrobacterium tumefaciens* LBA4404, and independent transgenic tobacco plants containing either a rice chitinase or alfalfa glucanase transgene were generated by the leaf disc method (see, e.g., Rogers et al., *Meth. in Enzymol.*, 118:627–640, 1986). Transformed plants were selected on Murashige and Skoog medium (see Murashige and Skoog, *Physiol. Plant*, 15:673, 1962) containing 200 µg/ml kanamycin and 500 µg/ml carbenicillin, and grown at 25° C. under a 16 hour light (115 mE)/8 hour dark cycle for several weeks. The seedlings from the transformed plants were then moved into soil.

Approximately 24 pBZ56 and 20 pM42X transgenic plants were confirmed as transformants by Southern blot hybridization. Expression of rice chitinase and alfalfa-glucanase transgenes was checked by conventional Northern blot and Western blot analysis. Several F2 generation transgenic lines that expressed high levels of either one of the above transgenes were selected for mating to produce an invention transgenic plant.

Preparation of Transgenic Tobacco Plant Containing Multiple Plant-Defense-Associated Genes The F2 high level expression homozygous transgenic lines of pBZ56 and pM42X transformants were crossed with each other using routine methods. Polymerase chain reaction (PCR) analysis was employed to confirm that the heterozygous F3 generation (i.e., crossed plants) contained both transgenes. After confirmation, the F3 generation seeds were harvested and F4 generation plants were produced. F4 generation plants that were homozygous for both the chitinase and glucanase transgenes were selected and their genotypes were confirmed by back-cross and PCR analysis. The F4 plants were used for fungal infection assays.

Preparation of Transgenic Rice Plant Containing Multiple Plant-Defense-Associated Genes The plasmid pBZ100 and a plasmid containing a hygromycin-resistant gene were introduced into rice embryos employing a commercially available ballistic micro-projectile device. The bombarded embryos were grown on N6 medium (see Chu et al., *Scientia Sinica*, 18:659–668, 1975) containing hygromycin. Regenerated hygromycin resistant plants were analyzed by PCR and Southern blot analysis for the presence of inheritable pBZ100 DNA. The results indicate that the genomic DNA of the rice transformants contain inheritable copies of both transgenes.

Assay for Resistance of Tobacco Transgenic Plants to *Cercospora Nicotinae* Fungal Infection Both F3 and F4 generation invention transgenic tobacco plants, described above, were subjected to the following fungal infection assay. The results are shown in FIGS. 3 and 4, respectively.

*Cercospora nicotianae* (available from American Type Culture Collection under ATCC Nos. 18366 and 18367) were cultured by suspending mycelial fragments in sterile ddH$_2$O. A tobacco leaf suspension was prepared containing 200 ml V8 juice, 3.0 g CaCO$_3$, 800 ml water, pH to 6.15, 18 g agar, 1 g dried tobacco leaves (dry several large leaves in the microwave for about 10 min or 'defrost'; grind in a mortar and pestle), and autoclaved for 20–25 minutes. Approximately 0.5–1.0 ml of the tobacco leaf suspension was spread onto a petri plate. The contents of the plate were incubated at 25° C. with continuous light for about 4–6 weeks until white-ish mycelial covered the plate evenly.

The F3 and F4 generations of an invention tobacco transgenic plant (approximately 100 of each), and appropriate controls, were grown to about 5–6 weeks old. Mycelia were cut evenly into small squares (approximately 2 mm$^2$) with a sterile scalpel. The mycelial agar squares were adhered to the underside and between the veins of tobacco leaves (not the newest leaf: usually the 2nd or 3rd from the top) using ¾" waterproof surgical tape (Blenderm, 3M). The plants were incubated at 20° C., for 4–10 days using a 16 hour daylength.

Symptoms of fungal infection become visible in approximately 24–96 hours. Initially, small pin-pricks are just visible, with perhaps some browning of the leaf tissue over the inoculum. This progresses to a grey-ish, dry lesion of increasing diameter. The relative level of fungal infection was scored using a numerical rating system as follows:

0—no symptoms, maybe a little browning;

1—'pin-pricks,' but no contiguous, measurable lesion;

>1—(measuring the lesions, taking the widest portion as one measurement, then the perpendicular as the other; multiply these to get an approximate disease area in mm$^2$)

FIG. 1 shows the results of the fungal infection assay for the F4 generation invention transgenic tobacco plants. The results indicate that the lesion sizes for the invention transgenic plant were at all times less than the lesion sizes observed for the controls, e.g., the wild type tobacco plant and the single-gene trangenic tobacco plants containing only one of either the chitinase or β-glucanase genes. Thus, the invention transgenic plant has a higher level of resistance to lesions caused by fungal pathogens than each of the control tobacco plants.

Figure 2:
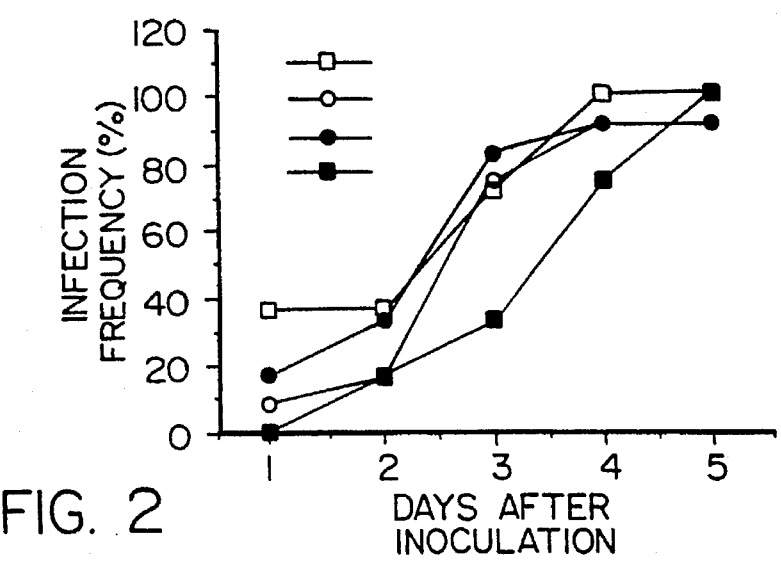
FIG. 2 shows the results of the *Cercospora nicotinae* fungal infection assay described in the Examples for the heterozygous F3 generation invention transgenic tobacco plants. □=wild type tobacco plant, o=chitinase transgenic tobacco plant, ●=glucanase transgenic tobacco plant, ■=chitinase/glucanase transgenic plant.

FIG. 2 shows the results of the fungal infection assay for the heterozygous F3 generation invention transgenic tobacco plants. The results indicate that the infection frequency for the invention transgenic tobacco plants was essentially less than the infection frequencies observed for the controls, e.g., the wild type tobacco plant and the single-gene trangenic tobacco plants containing only one of either the chitinase or β-glucanase genes. Thus, the invention transgenic plant has a higher level of resistance to fungal infection caused by fungal pathogens than each of the control tobacco plants.

Assay for Resistance of Tobacco Transgenic Plants to *Thanatephorus Cucumeris* Fungal Infection In the imperfect stage, *T. cucumeris* from anastomosis group 3 (such as the strain ATCC No. 62149) causes stem lesions ("sore shin") similar to the pathogen *Rhizoctonia solani*. However, basidiospores of the fungus form in the perfect stage. Germinating basidiospores form appressoria that penetrate tobacco leaves directly, leading to the formation of lesions ('target spot'). Factors that favor development of the perfect stage are temperatures within the range of 16°–28° C. and leaf wetness.

*T. cucumeris* were cultured by inoculating autoclaved rice media (50 g Uncle Ben's Converted Rice, 25 ml doubly distilled water in 250 ml flasks; cover with foil and autoclave 25 minutes, see Shew and Main, *Plant Disease,* 74:1009–1013, 1990) with squares of mycelia from PDA (potato dextrose agar) plates. The plates were incubated at 22°–25° C. for 2–4 weeks with continuous light (the rice looks "mummified'- - - white and powdery).

To inoculate the invention transgenic tobacco plant, and appropriate controls, inoculum was ground in a blender until very few rice grains remained (approximately 3×45 seconds, scraping down the sides in between). Starting with the 0 level, inoculum was mixed into dry potting mix at the rate of 0, 1, 2 and 5 g rice mixture/liter of soil and distributed to 9-well pot forms. Eighteen 4–5 week old tobacco seedlings were transplanted to the wells, being careful to avoid carryover from high inoculum levels to low ones (preferably use the wooden end of a separate disposable cotton applicator for each level to make a hole and firm the soil around the stem). Subsequently, pot-sets were placed in a flat cover with a plastic dome and incubated at 20° C. for 4–7 days using a 16 hour daylength. The dome was removed and sprinkled with water as needed to maintain moist conditions.

Symptoms of fungal infection in the highest inoculum become evident in approximately 3–4 days. Leaves touching the soil become grey-ish and wilted; upper leaves wilt; stems become girdled at the soil line, brown-ish and constricted. For the results shown in FIGS. 3A and B, the relative level of fungal infection was scored using a numerical rating system as follows:

0—No symptoms;

1—A diseased leaf or wilting, but plant may survive;

2—Severely constricted stem indicating plant will die; flat-out, wilted plant.

Figure 3A:
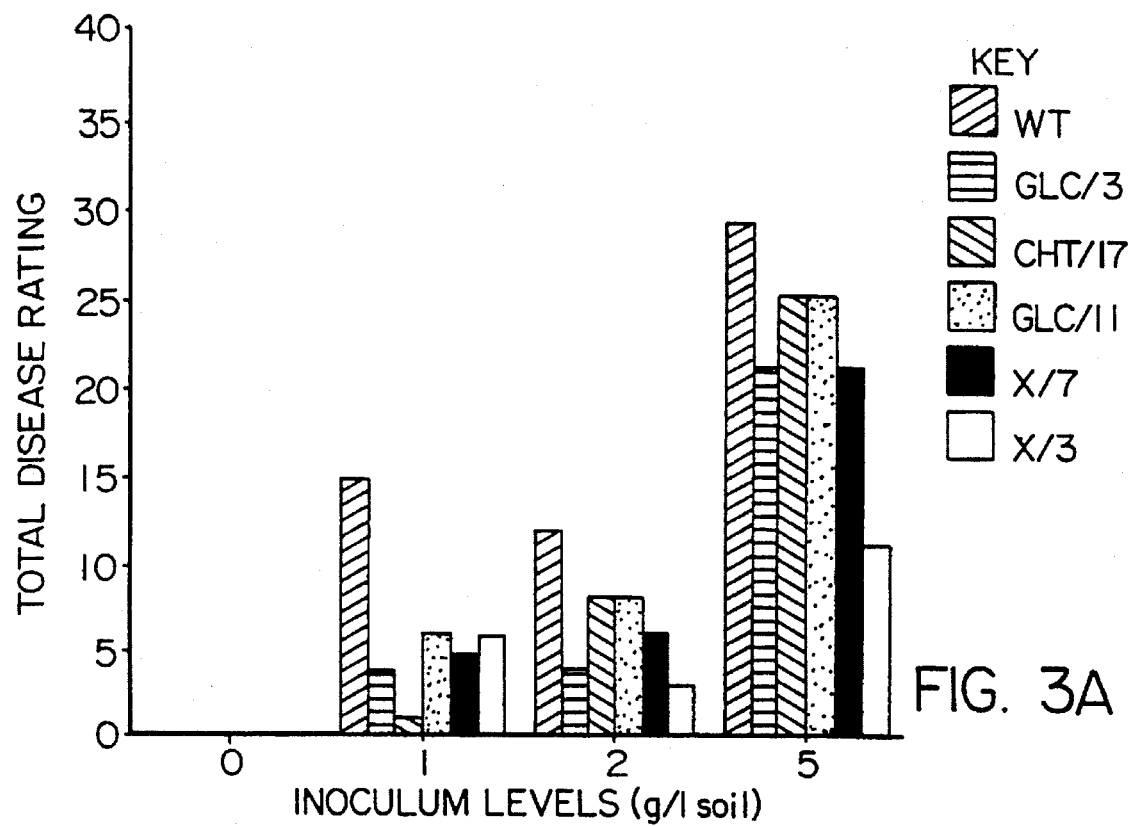
FIGS. 3A (day 4 data) and 3B (day 5 data) show the results of one of the *Thanatephorus cucumeris* fungal infection assays described in the Examples. The key in descending order corresponds to each cluster of bars from left to right on the bar graph. WT=wild type tobacco plant; GLC/3 and GLC/11=are glucanase transgenic tobacco plants; Cht/17=chitinase transgenic tobacco plant; X/7 and X/3 are chitinase/glucanase transgenic tobacco plants.
Figure 3B:
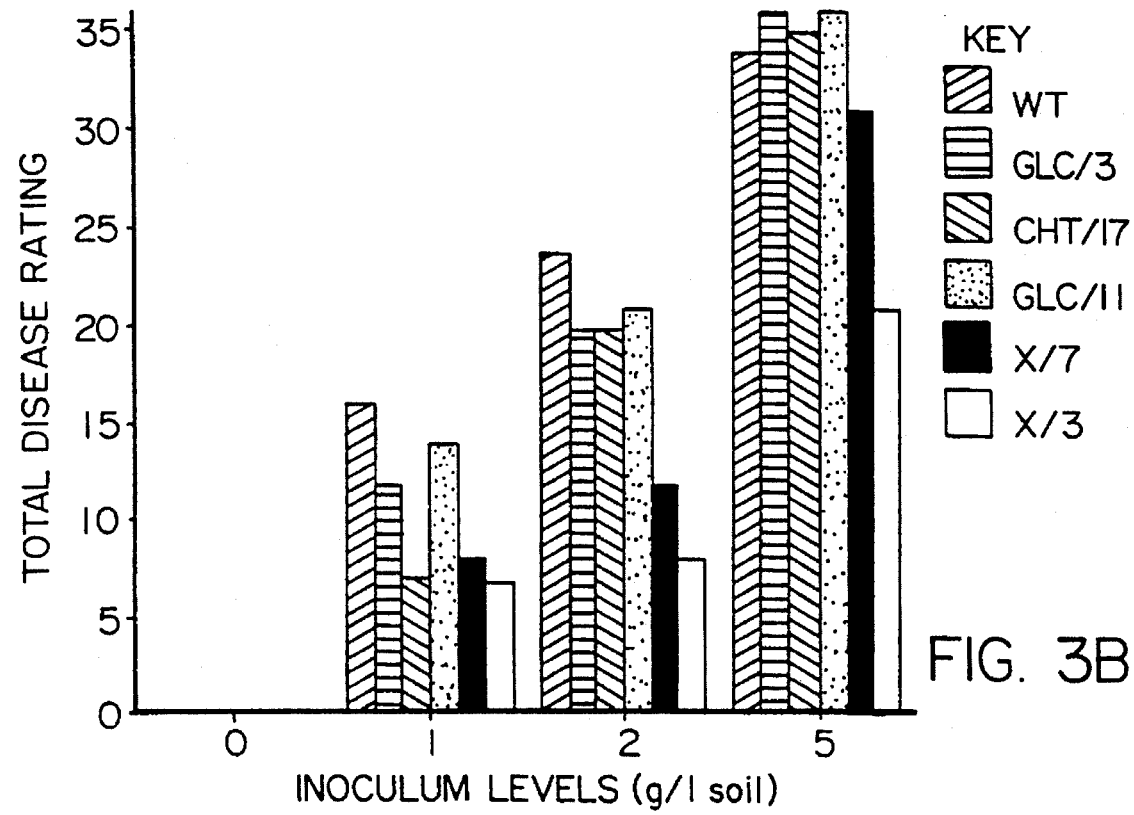

The results of the assay at days 4 and 5 are shown in FIGS. 3A and 3B, respectively. FIG. 3A (day 4) indicates that the invention transgenic plant designated X/3, when grown in potting soil containing 5 g of the above-described fungal rice mixture/liter, has a higher level of resistance to the pathogen than the control tobacco plants which include a wild type tobacco plant and single-gene trangenic tobacco plants containing either one of the chitinase or β-glucanase gene.

FIG. 3B (day 5) indicates that both the X/7 and X/3 invention transgenic tobacco plants, when grown in potting soil containing 2 g and 5 g of rice mixture/liter, have a higher level of resistance to the pathogen than the control tobacco plants which include a wild type tobacco plant and single-gene trangenic tobacco plants containing either one of the chitinase or β-glucanase gene.

Figure 4A:
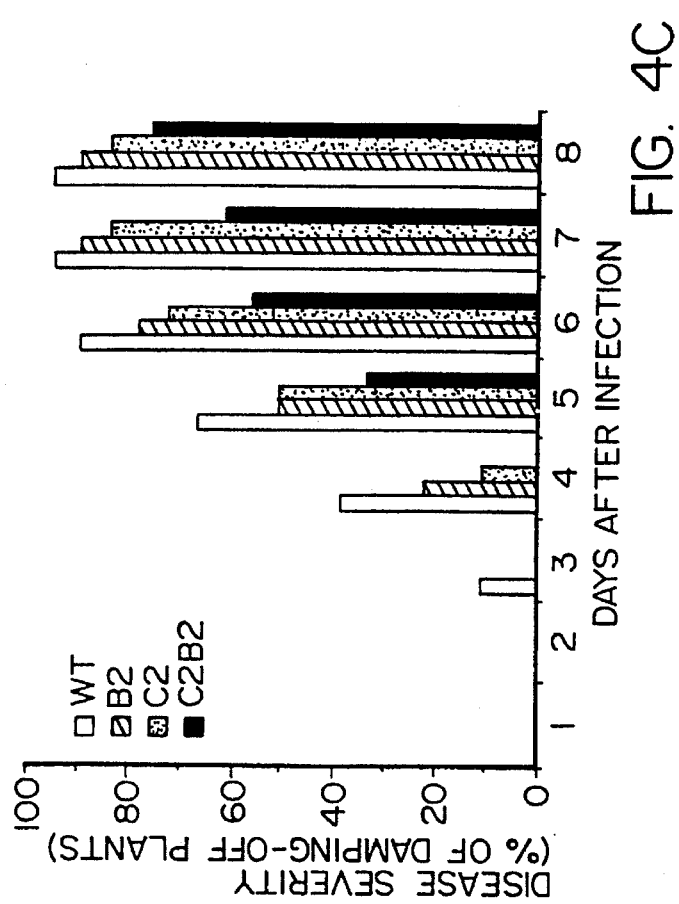
FIGS. 4A, 4B, and 4C show the results of one of the *Thanatephorus cucumeris* fungal infection assays described in the Examples. The key in descending order corresponds to each cluster of bars from left to right on the bar graph. WT = wild type tobacco plant; B2=glucanase transgenic tobacco plant; C2=chitinase transgenic tobacco plant; and C2B2= chitinase/glucanase transgenic tobacco plant.
Figure 4B:
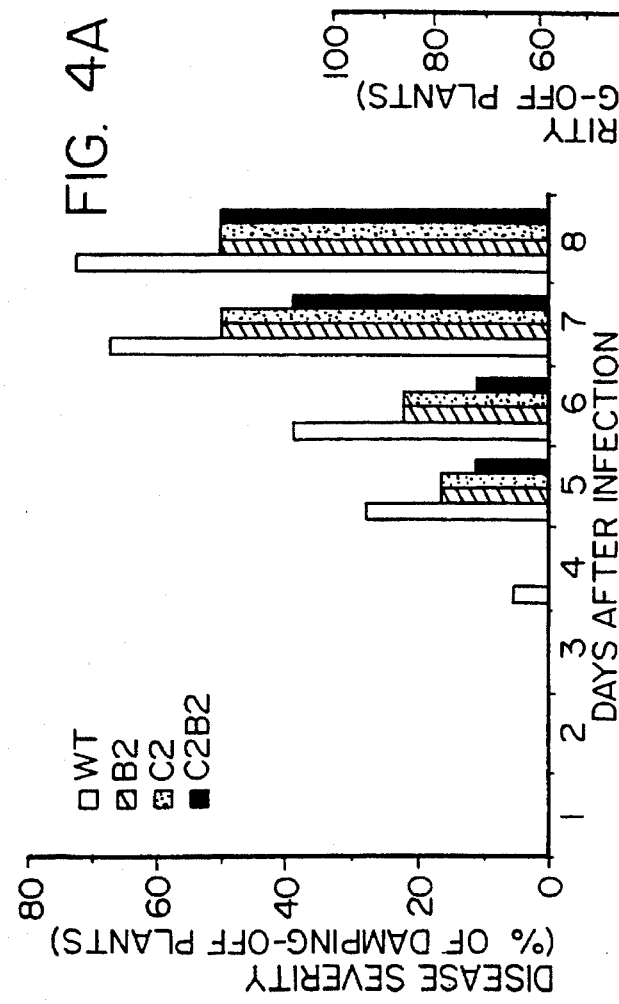
Figure 4C:
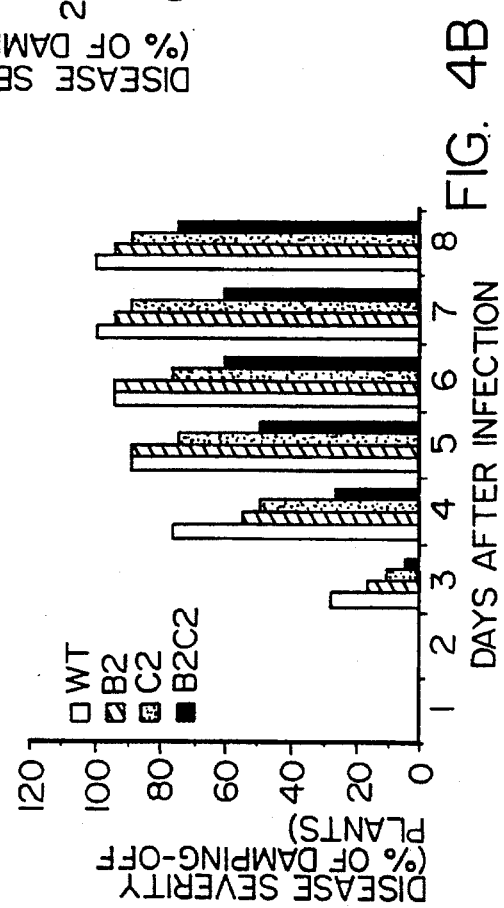

A similar assay was conducted using F5 transgenic tobacco plants that were homozygous for both the chitinase and β-glucanase genes. In this assay 4 g, 15 g, and 45 g of the rice mixture/liter was employed, and the plants were scored as either healthy or diseased. The results are shown in FIGS. 4A (4 g), 4B (15 g), and 4C (45 g). The results indicate that the invention transgenic plant containing two plant-defense-associated proteins clearly has increased resistance to fungal pathogens relative to non-transgenic plants and transgenic plants of the same species that only express one of said plant-defense-associated proteins.

While the invention has been described in detail with reference to certain preferred embodiments thereof, it will be understood that modifications and variations are within the spirit and scope of that which is described and claimed.

That which is claimed is:

1. A transgenic plant comprising:
a first exogenous transgene encoding an overexpressed and biologically active rice chitinase protein; and
a second exogenous transgene encoding an overexpressed and biologically active alfalfa glucanase protein,
wherein:
said transgenes are constitutively expressed, and
said plant has increased resistance to fungal pathogens relative to plants that do not constitutively express both of said transgenes.

2. A plant according to claim 1, wherein said plant is a tobacco plant.

3. A nucleic acid construct comprising:
a first transgene encoding a biologically active rice chitinase protein; and
a second transgene encoding a biologically active alfalfa glucanase protein, and
wherein each of said transgenes are operatively linked to a plant-functional promoter.

4. A construct according to claim 3, wherein said promoter is a constitutive promoter.

5. A construct according to claim 3, wherein said construct imparts to transgenic plants containing same, increased resistance to fungal pathogens relative to non-transgenic plants of the same species that do not contain said construct.

6. A vector comprising the construct of claim 3.

7. A plant cell containing the vector of claim 6.

8. A method to increase fungal disease resistance of a plant, said method comprising:

introducing the nucleic acid construct of claim 3 into the genome of said plant.

9. A method to increase fungal disease resistance of a transgenic plant containing a transgene encoding a biologically active rice chitinase protein, said method comprising:

introducing a transgene encoding a biologically active alfalfa glucanase protein into the genome of said plant, wherein at least one transgene is heterologous to said plant.

10. A method to increase fungal disease resistance of a transgenic plant containing a transgene encoding a biologically active alfalfa glucanase protein, said method comprising:

introducing a transgene encoding a biologically active rice chitinase protein into the genome of said plant, wherein at least one transgene is heterologous to said plant.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:

(A) LENGTH: 1151 base pairs
(B) TYPE: nucleic acid
(C) STRANDEDNESS: both
(D) TOPOLOGY: both (ii) MOLECULE TYPE: cDNA (ix) FEATURE:
(A) NAME/KEY: CDS
(B) LOCATION: 55..1062
(D) OTHER INFORMATION: /product="RICE CHITINASE"

(xi) SEQUENCE DESCRIPTION: SEQ ID NO:1:

```
AATCAGTCAA TCTGTATACA GCAACTCAGC GATCTTATAT TTACCCAACA CACC ATG        57
                                                              Met
                                                              1

AGA GCG CTC GCT GTG GTG GCC ATG GTG GCC AGG CCC TTC CTC GCG GCG       105
Arg Ala Leu Ala Val Val Ala Met Val Ala Arg Pro Phe Leu Ala Ala
            5               10                  15

GCC GTG CAT GCC GAG CAG TGC GGC AGC CAG GCC GGC GGC GCG GTG TGC       153
Ala Val His Ala Glu Gln Cys Gly Ser Gln Ala Gly Gly Ala Val Cys
        20              25                  30

CCC AAC TGC CTC TGC TGC AGC CAG TTC GGC TGG TGC GGC TCC ACC TCC       201
Pro Asn Cys Leu Cys Cys Ser Gln Phe Gly Trp Cys Gly Ser Thr Ser
    35              40                  45

GAC TAC TGC GGC GCC GGA TGC CAG AGC CAG TGC TCG CGG CTG CGG CGG       249
Asp Tyr Cys Gly Ala Gly Cys Gln Ser Gln Cys Ser Arg Leu Arg Arg
50              55                  60                      65

CGG CGG CCC GAC GCG TCC GGC GGC GGT GGC AGC GGC GTC GCG TCC ATC       297
Arg Arg Pro Asp Ala Ser Gly Gly Gly Gly Ser Gly Val Ala Ser Ile
                70                  75                  80

GTG TCG CGC TCG CTC TTC GAC CTG ATG CTG CTC CAC CGC AAC GAT GCG       345
Val Ser Arg Ser Leu Phe Asp Leu Met Leu Leu His Arg Asn Asp Ala
            85                  90                  95

GCG TGC CCG GCC AGC AAC TTC TAC ACC TAC GAC GCC TTC GTC GCC GCC       393
Ala Cys Pro Ala Ser Asn Phe Tyr Thr Tyr Asp Ala Phe Val Ala Ala
        100                 105                 110

GCC AGC GCC TTC CCG GGC TTC GCC GCC GCG GGC GAC GCC GAC ACC AAC       441
Ala Ser Ala Phe Pro Gly Phe Ala Ala Ala Gly Asp Ala Asp Thr Asn
    115                 120                 125

AAG CGC GAG GTC GCC GCG TTC CTT GCG CAG ACG TCC CAC GAG ACC ACC       489
Lys Arg Glu Val Ala Ala Phe Leu Ala Gln Thr Ser His Glu Thr Thr
130                 135                 140                 145

GGC GGG TGG GCG ACG GCG CCC GAC GGC CCC TAC ACG TGG GGC TAC TGC       537
Gly Gly Trp Ala Thr Ala Pro Asp Gly Pro Tyr Thr Trp Gly Tyr Cys
                150                 155                 160

TTC AAG GAG GAG AAC GGC GGC GCC GGG CCG GAC TAC TGC CAG CAG AGC       585
Phe Lys Glu Glu Asn Gly Gly Ala Gly Pro Asp Tyr Cys Gln Gln Ser
            165                 170                 175

GCG CAG TGG CCG TGC GCC GCC GGC AAG AAG TAC TAC GGC CGG GGT CCC       633
Ala Gln Trp Pro Cys Ala Ala Gly Lys Lys Tyr Tyr Gly Arg Gly Pro
        180                 185                 190

ATC CAG CTC TCC TAC AAC TTC AAC TAC GGG CCG GCG GGG CAG GCC ATC       681
Ile Gln Leu Ser Tyr Asn Phe Asn Tyr Gly Pro Ala Gly Gln Ala Ile
    195                 200                 205

GGC GCC GAC CTG CTC GGC GAC CCG GAC CTC GTG GCG TCT GAC GCC ACC       729
Gly Ala Asp Leu Leu Gly Asp Pro Asp Leu Val Ala Ser Asp Ala Thr
210                 215                 220                 225

GTC TCC TTC GAC ACG GCC TTC TGG TTC TGG ATG ACG CCG CAG TCG CCC       777
Val Ser Phe Asp Thr Ala Phe Trp Phe Trp Met Thr Pro Gln Ser Pro
                230                 235                 240

AAG CCG TCG TGC AAC GCG GTC GCC ACC GGC CAG TGG ACG CCC TCC GCC       825
Lys Pro Ser Cys Asn Ala Val Ala Thr Gly Gln Trp Thr Pro Ser Ala
```

|     |     |     |     |     |     |     |     |     |     |     |     |     |     |     |     |       |
| --- | --- | --- | --- | --- | --- | --- | --- | --- | --- | --- | --- | --- | --- | --- | --- | ----- |
|     |     |     | 245 |     |     |     |     | 250 |     |     |     |     | 255 |     |     |       |
| GAC | GAC | CAG | CGG | GCG | GGC | CGC | GTG | CCG | GGC | TAC | GGC | GTC | ATC | ACC | AAC | 873   |
| Asp | Asp | Gln | Arg | Ala | Gly | Arg | Val | Pro | Gly | Tyr | Gly | Val | Ile | Thr | Asn |       |
|     |     | 260 |     |     |     |     | 265 |     |     |     |     | 270 |     |     |     |       |
| ATC | ATC | AAC | GGC | GGG | CTG | GAG | TGC | GGC | CAT | GGC | GAG | GAC | GAT | CGC | ATC | 921   |
| Ile | Ile | Asn | Gly | Gly | Leu | Glu | Cys | Gly | His | Gly | Glu | Asp | Asp | Arg | Ile |       |
|     | 275 |     |     |     |     | 280 |     |     |     |     | 285 |     |     |     |     |       |
| GCC | GAC | CGG | ATC | GGC | TTC | TAC | AAG | CGC | TAC | TGC | GAC | ATC | CTC | GGC | GTC | 969   |
| Ala | Asp | Arg | Ile | Gly | Phe | Tyr | Lys | Arg | Tyr | Cys | Asp | Ile | Leu | Gly | Val |       |
| 290 |     |     |     |     | 295 |     |     |     |     | 300 |     |     |     |     | 305 |       |
| AGC | TAC | GGC | GCC | AAC | TTG | GAT | TGC | TAC | AGC | CAG | AGG | CCT | TCG | GCT | CCT | 1017  |
| Ser | Tyr | Gly | Ala | Asn | Leu | Asp | Cys | Tyr | Ser | Gln | Arg | Pro | Ser | Ala | Pro |       |
|     |     |     |     | 310 |     |     |     |     | 315 |     |     |     |     | 320 |     |       |
| CCT | AAG | CTT | CGC | CTA | CCT | AGC | TTC | CAC | ACA | GTG | ATA | AAT | AAT | CAC |     | 1062  |
| Pro | Lys | Leu | Arg | Leu | Pro | Ser | Phe | His | Thr | Val | Ile | Asn | Asn | His |     |       |
|     |     |     | 325 |     |     |     |     | 330 |     |     |     |     | 335 |     |     |       |

TGATGGAGTA TAGTTTACAC CATATCGATG AATAAAACTT GATCCGAATT CTCGCCCTAT 1122

AGTGAGTCGT ATTAGTCGAC AGCTCTAGA 1151

( 2 ) INFORMATION FOR SEQ ID NO:2:

( i ) SEQUENCE CHARACTERISTICS:
        ( A ) LENGTH: 336 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | Arg | Ala | Leu | Ala | Val | Val | Ala | Met | Val | Ala | Arg | Pro | Phe | Leu | Ala |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |     |
| Ala | Ala | Val | His | Ala | Glu | Gln | Cys | Gly | Ser | Gln | Ala | Gly | Gly | Ala | Val |
|     |     |     | 20  |     |     |     |     | 25  |     |     |     |     | 30  |     |     |
| Cys | Pro | Asn | Cys | Leu | Cys | Cys | Ser | Gln | Phe | Gly | Trp | Cys | Gly | Ser | Thr |
|     |     | 35  |     |     |     |     | 40  |     |     |     |     | 45  |     |     |     |
| Ser | Asp | Tyr | Cys | Gly | Ala | Gly | Cys | Gln | Ser | Gln | Cys | Ser | Arg | Leu | Arg |
|     | 50  |     |     |     |     | 55  |     |     |     |     | 60  |     |     |     |     |
| Arg | Arg | Arg | Pro | Asp | Ala | Ser | Gly | Gly | Gly | Gly | Ser | Gly | Val | Ala | Ser |
| 65  |     |     |     |     | 70  |     |     |     |     | 75  |     |     |     |     | 80  |
| Ile | Val | Ser | Arg | Ser | Leu | Phe | Asp | Leu | Met | Leu | Leu | His | Arg | Asn | Asp |
|     |     |     |     | 85  |     |     |     |     | 90  |     |     |     |     | 95  |     |
| Ala | Ala | Cys | Pro | Ala | Ser | Asn | Phe | Tyr | Thr | Tyr | Asp | Ala | Phe | Val | Ala |
|     |     |     | 100 |     |     |     |     | 105 |     |     |     |     | 110 |     |     |
| Ala | Ala | Ser | Ala | Phe | Pro | Gly | Phe | Ala | Ala | Ala | Gly | Asp | Ala | Asp | Thr |
|     |     | 115 |     |     |     |     | 120 |     |     |     |     | 125 |     |     |     |
| Asn | Lys | Arg | Glu | Val | Ala | Ala | Phe | Leu | Ala | Gln | Thr | Ser | His | Glu | Thr |
|     | 130 |     |     |     |     | 135 |     |     |     |     | 140 |     |     |     |     |
| Thr | Gly | Gly | Trp | Ala | Thr | Ala | Pro | Asp | Gly | Pro | Tyr | Thr | Trp | Gly | Tyr |
| 145 |     |     |     |     | 150 |     |     |     |     | 155 |     |     |     |     | 160 |
| Cys | Phe | Lys | Glu | Glu | Asn | Gly | Gly | Ala | Gly | Pro | Asp | Tyr | Cys | Gln | Gln |
|     |     |     |     | 165 |     |     |     |     | 170 |     |     |     |     | 175 |     |
| Ser | Ala | Gln | Trp | Pro | Cys | Ala | Ala | Gly | Lys | Lys | Tyr | Tyr | Gly | Arg | Gly |
|     |     |     | 180 |     |     |     |     | 185 |     |     |     |     | 190 |     |     |
| Pro | Ile | Gln | Leu | Ser | Tyr | Asn | Phe | Asn | Tyr | Gly | Pro | Ala | Gly | Gln | Ala |
|     |     | 195 |     |     |     |     | 200 |     |     |     |     | 205 |     |     |     |
| Ile | Gly | Ala | Asp | Leu | Leu | Gly | Asp | Pro | Asp | Leu | Val | Ala | Ser | Asp | Ala |
|     | 210 |     |     |     |     | 215 |     |     |     |     | 220 |     |     |     |     |

```
Thr  Val  Ser  Phe  Asp  Thr  Ala  Phe  Trp  Phe  Trp  Met  Thr  Pro  Gln  Ser
225            230                      235                           240

Pro  Lys  Pro  Ser  Cys  Asn  Ala  Val  Ala  Thr  Gly  Gln  Trp  Thr  Pro  Ser
                    245                      250                      255

Ala  Asp  Asp  Gln  Arg  Ala  Gly  Arg  Val  Pro  Gly  Tyr  Gly  Val  Ile  Thr
               260                      265                      270

Asn  Ile  Ile  Asn  Gly  Gly  Leu  Glu  Cys  Gly  His  Gly  Glu  Asp  Asp  Arg
          275                      280                      285

Ile  Ala  Asp  Arg  Ile  Gly  Phe  Tyr  Lys  Arg  Tyr  Cys  Asp  Ile  Leu  Gly
     290                      295                      300

Val  Ser  Tyr  Gly  Ala  Asn  Leu  Asp  Cys  Tyr  Ser  Gln  Arg  Pro  Ser  Ala
305                      310                      315                      320

Pro  Pro  Lys  Leu  Arg  Leu  Pro  Ser  Phe  His  Thr  Val  Ile  Asn  Asn  His
                    325                      330                      335
```

( 2 ) INFORMATION FOR SEQ ID NO:3:

( i ) SEQUENCE CHARACTERISTICS:
    ( A ) LENGTH: 1374 base pairs
    ( B ) TYPE: nucleic acid
    ( C ) STRANDEDNESS: both
    ( D ) TOPOLOGY: both ( i i ) MOLECULE TYPE: cDNA ( i x ) FEATURE:
    ( A ) NAME/KEY: CDS
    ( B ) LOCATION: 52..1158
    ( D ) OTHER INFORMATION: /product="ALFALFA BETA-GLUCANASE"

( x i ) SEQUENCE DESCRIPTION: SEQ ID NO:3:

```
CGGCAAATCC TTCTTTCATA TTCATTTTTA GTGTATACTT TATTTGCAT C ATG CCT              57
                                                       Met Pro
                                                         1

TCT  TTC  TTT  GCT  CCA  ACC  AGG  AGG  TTC  TCC  TTG  GCT  TCT  CCT  CTC  CTT   105
Ser  Phe  Phe  Ala  Pro  Thr  Arg  Arg  Phe  Ser  Leu  Ala  Ser  Pro  Leu  Leu
               5                        10                       15

CTA  TTG  GGA  TTG  TTC  ACA  ATA  AAC  CTC  ATT  CCC  ACA  GCA  GAT  GCT  CAA   153
Leu  Leu  Gly  Leu  Phe  Thr  Ile  Asn  Leu  Ile  Pro  Thr  Ala  Asp  Ala  Gln
          20                       25                       30

ATA  GGA  GTA  TGT  TAT  GGT  ATG  ATG  GGA  AAC  AAT  CTA  CCA  CCA  GCA  AAC   201
Ile  Gly  Val  Cys  Tyr  Gly  Met  Met  Gly  Asn  Asn  Leu  Pro  Pro  Ala  Asn
35                       40                       45                       50

GAA  GTT  ATA  GAT  CTC  TAC  AAA  GCA  AAC  AAC  ATT  AAG  AGA  ATG  AGA  CTC   249
Glu  Val  Ile  Asp  Leu  Tyr  Lys  Ala  Asn  Asn  Ile  Lys  Arg  Met  Arg  Leu
               55                       60                       65

TAT  GAT  CCT  AAT  CAA  GCT  GCT  CTA  AAT  GCA  TTA  AGA  AAT  TCA  GGC  ATT   297
Tyr  Asp  Pro  Asn  Gln  Ala  Ala  Leu  Asn  Ala  Leu  Arg  Asn  Ser  Gly  Ile
          70                       75                       80

GAA  CTC  ATT  CTT  GGT  GTG  CCT  AAT  TCC  GAC  CTT  CAA  AGC  CTA  GCC  ACC   345
Glu  Leu  Ile  Leu  Gly  Val  Pro  Asn  Ser  Asp  Leu  Gln  Ser  Leu  Ala  Thr
          85                       90                       95

AAC  TCT  GAT  AAT  GCA  CGT  CAA  TGG  GTA  CAA  AGA  AAT  GTA  TTG  AAT  TTC   393
Asn  Ser  Asp  Asn  Ala  Arg  Gln  Trp  Val  Gln  Arg  Asn  Val  Leu  Asn  Phe
          100                      105                      110

TGG  CCT  AGT  GTC  AAA  ATC  AAG  TAT  ATT  GCA  GTT  GGT  AAT  GAA  GTG  AGT   441
Trp  Pro  Ser  Val  Lys  Ile  Lys  Tyr  Ile  Ala  Val  Gly  Asn  Glu  Val  Ser
115                      120                      125                      130

CCA  GTT  GGA  GGT  TCT  TCT  TGG  CTA  GGA  CAA  TAT  GTT  TTA  CCT  GCC  ACC   489
Pro  Val  Gly  Gly  Ser  Ser  Trp  Leu  Gly  Gln  Tyr  Val  Leu  Pro  Ala  Thr
               135                      140                      145

CAA  AAT  ATA  TAT  CAA  GCT  ATA  AGA  GCT  AAA  AAT  CTT  CAT  GAT  CAA  ATC   537
```

| | | | | | | | | | | | | | | | | |
|---|---|---|---|---|---|---|---|---|---|---|---|---|---|---|---|---|
| Gln | Asn | Ile | Tyr<br>150 | Gln | Ala | Ile | Arg | Ala<br>155 | Lys | Asn | Leu | His | Asp<br>160 | Gln | Ile | |
| TTG | GTT | TCA | ACC | GCT | ATT | GAC | ATG | ACC | CTT | ATT | GGA | AAC | TCA | TTC | CCT | 585 |
| Leu | Val | Ser<br>165 | Thr | Ala | Ile | Asp | Met<br>170 | Thr | Leu | Ile | Gly | Asn<br>175 | Ser | Phe | Pro | |
| CCA | TCT | AAA | GGT | TCT | TTC | AGA | AAT | GAT | GTT | AGG | GCA | TAC | CTA | GAT | CCT | 633 |
| Pro | Ser<br>180 | Lys | Gly | Ser | Phe | Arg<br>185 | Asn | Asp | Val | Arg | Ala<br>190 | Tyr | Leu | Asp | Pro | |
| TTT | ATT | GGA | TAC | TTG | GTA | TAT | GCA | GGT | GCA | CCT | TTA | CTT | GTC | AAT | GTT | 681 |
| Phe<br>195 | Ile | Gly | Tyr | Leu | Val<br>200 | Tyr | Ala | Gly | Ala | Pro<br>205 | Leu | Leu | Val | Asn | Val<br>210 | |
| TAC | CCT | TAT | TTT | AGC | CAT | GTT | GGT | AAC | CCG | CGC | GAC | ATA | TCT | CTT | CCT | 729 |
| Tyr | Pro | Tyr | Phe | Ser<br>215 | His | Val | Gly | Asn | Pro<br>220 | Arg | Asp | Ile | Ser | Leu<br>225 | Pro | |
| TAT | GCT | CTT | TTC | ACT | TCA | CCG | GGT | GTT | ATG | GTA | CAA | GAC | GGT | CCA | AAT | 777 |
| Tyr | Ala | Leu | Phe<br>230 | Thr | Ser | Pro | Gly | Val<br>235 | Met | Val | Gln | Asp | Gly<br>240 | Pro | Asn | |
| GGG | TAC | CAA | AAC | TTG | TTT | GAT | GCT | ATG | TTG | GAT | TCG | GTG | CAT | GCA | GCC | 825 |
| Gly | Tyr | Gln<br>245 | Asn | Leu | Phe | Asp | Ala<br>250 | Met | Leu | Asp | Ser | Val<br>255 | His | Ala | Ala | |
| CTA | GAT | AAC | ACT | GGG | ATT | GGT | TGG | GTG | AAC | GTT | GTT | GTA | TCT | GAG | AGT | 873 |
| Leu | Asp | Asn<br>260 | Thr | Gly | Ile | Gly<br>265 | Trp | Val | Asn | Val | Val<br>270 | Val | Ser | Glu | Ser | |
| GGT | TGG | CCC | TCT | GAT | GGA | GGC | GCT | ACT | TCA | TAT | GAC | AAC | GCA | CGT | ATT | 921 |
| Gly<br>275 | Trp | Pro | Ser | Asp | Gly<br>280 | Gly | Ala | Thr | Ser | Tyr<br>285 | Asp | Asn | Ala | Arg | Ile<br>290 | |
| TAT | CTT | GAT | AAT | TTG | ATT | CGT | TAT | GAA | GGT | AAA | GGT | ACT | CCA | AGA | AGG | 969 |
| Tyr | Leu | Asp | Asn | Leu<br>295 | Ile | Arg | Tyr | Glu | Gly<br>300 | Lys | Gly | Thr | Pro | Arg<br>305 | Arg | |
| CCT | TGG | GCT | ACA | GAA | ACT | TAT | ATT | TTT | GCT | ATG | TTT | GAT | GAG | AAC | CAA | 1017 |
| Pro | Trp | Ala | Thr<br>310 | Glu | Thr | Tyr | Ile | Phe<br>315 | Ala | Met | Phe | Asp | Glu<br>320 | Asn | Gln | |
| AAG | AGT | CCA | GAA | TTG | GAG | AAA | CAT | TTT | GGA | GTG | TTT | TAT | CCT | AAT | AAA | 1065 |
| Lys | Ser | Pro<br>325 | Glu | Leu | Glu | Lys | His<br>330 | Phe | Gly | Val | Phe | Tyr<br>335 | Pro | Asn | Lys | |
| CAA | AAG | AAG | TAC | CCA | TTT | GGA | TTT | GGT | GGG | GAA | AGA | ATG | GGA | ATT | GTC | 1113 |
| Gln | Lys<br>340 | Lys | Tyr | Pro | Phe | Gly<br>345 | Phe | Gly | Gly | Glu | Arg<br>350 | Met | Gly | Ile | Val | |
| AAT | GGT | GAC | TTC | AAT | GCA | ACT | ATT | TCT | CTT | AAG | AGT | GAC | ATG | TAAGAAAAA | | 1165 |
| Asn | Gly<br>355 | Asp | Phe | Asn | Ala<br>360 | Thr | Ile | Ser | Leu | Lys<br>365 | Ser | Asp | Met | | | |

| | | | | |
|---|---|---|---|---|
| ATCAAGGTTT | TCAAGATTTG | AGTGGTTTTA | TGCATAAAAT | AAGAGAATTT CTCGTGTATG | 1225 |
| TATTTTATTT | ATCTTTCTTT | TTTCGGGTGT | AGAAATTTG | GAATGCTTGA GTTTCCTATT | 1285 |
| TCTCTAAAAA | TTAATGTCTT | GTGATGAAGT | TATATGAATA | TTTATATAAA GCGTAACTTT | 1345 |
| CCAAATTATT | TAATACTATT | TTTCAAAAA | | | 1374 |

( 2 ) INFORMATION FOR SEQ ID NO:4:

( i ) SEQUENCE CHARACTERISTICS:
        ( A ) LENGTH: 368 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| | | | | | | | | | | | | | | |
|---|---|---|---|---|---|---|---|---|---|---|---|---|---|---|
| Met<br>1 | Pro | Ser | Phe | Phe<br>5 | Ala | Pro | Thr | Arg | Arg<br>10 | Phe | Ser | Leu | Ala | Ser<br>15 | Pro |
| Leu | Leu | Leu | Leu<br>20 | Gly | Leu | Phe | Thr | Ile<br>25 | Asn | Leu | Ile | Pro | Thr<br>30 | Ala | Asp |

| | | | | | | | | | | | | | | |
|---|---|---|---|---|---|---|---|---|---|---|---|---|---|---|
| Ala | Gln | Ile 35 | Gly | Val | Cys | Tyr | Gly 40 | Met | Met | Gly | Asn | Asn 45 | Leu | Pro | Pro |
| Ala | Asn | Glu 50 | Val | Ile | Asp | Leu 55 | Tyr | Lys | Ala | Asn | Asn 60 | Ile | Lys | Arg | Met |
| Arg 65 | Leu | Tyr | Asp | Pro | Asn 70 | Gln | Ala | Ala | Leu | Asn 75 | Ala | Leu | Arg | Asn | Ser 80 |
| Gly | Ile | Glu | Leu | Ile 85 | Leu | Gly | Val | Pro | Asn 90 | Ser | Asp | Leu | Gln | Ser 95 | Leu |
| Ala | Thr | Asn | Ser 100 | Asp | Asn | Ala | Arg | Gln 105 | Trp | Val | Gln | Arg | Asn 110 | Val | Leu |
| Asn | Phe | Trp 115 | Pro | Ser | Val | Lys | Ile 120 | Lys | Tyr | Ile | Ala | Val 125 | Gly | Asn | Glu |
| Val | Ser 130 | Pro | Val | Gly | Gly | Ser 135 | Ser | Trp | Leu | Gly | Gln 140 | Tyr | Val | Leu | Pro |
| Ala 145 | Thr | Gln | Asn | Ile | Tyr 150 | Gln | Ala | Ile | Arg | Ala 155 | Lys | Asn | Leu | His | Asp 160 |
| Gln | Ile | Leu | Val | Ser 165 | Thr | Ala | Ile | Asp | Met 170 | Thr | Leu | Ile | Gly | Asn 175 | Ser |
| Phe | Pro | Pro | Ser 180 | Lys | Gly | Ser | Phe | Arg 185 | Asn | Asp | Val | Arg | Ala 190 | Tyr | Leu |
| Asp | Pro | Phe 195 | Ile | Gly | Tyr | Leu | Val 200 | Tyr | Ala | Gly | Ala | Pro 205 | Leu | Leu | Val |
| Asn | Val 210 | Tyr | Pro | Tyr | Phe | Ser 215 | His | Val | Gly | Asn | Pro 220 | Arg | Asp | Ile | Ser |
| Leu 225 | Pro | Tyr | Ala | Leu | Phe 230 | Thr | Ser | Pro | Gly | Val 235 | Met | Val | Gln | Asp | Gly 240 |
| Pro | Asn | Gly | Tyr | Gln 245 | Asn | Leu | Phe | Asp | Ala 250 | Met | Leu | Asp | Ser | Val 255 | His |
| Ala | Ala | Leu | Asp 260 | Asn | Thr | Gly | Ile | Gly 265 | Trp | Val | Asn | Val | Val 270 | Val | Ser |
| Glu | Ser | Gly 275 | Trp | Pro | Ser | Asp | Gly 280 | Gly | Ala | Thr | Ser | Tyr 285 | Asp | Asn | Ala |
| Arg | Ile 290 | Tyr | Leu | Asp | Asn | Leu 295 | Ile | Arg | Tyr | Glu | Gly 300 | Lys | Gly | Thr | Pro |
| Arg 305 | Arg | Pro | Trp | Ala | Thr 310 | Glu | Thr | Tyr | Ile | Phe 315 | Ala | Met | Phe | Asp | Glu 320 |
| Asn | Gln | Lys | Ser | Pro 325 | Glu | Leu | Glu | Lys | His 330 | Phe | Gly | Val | Phe | Tyr 335 | Pro |
| Asn | Lys | Gln | Lys 340 | Lys | Tyr | Pro | Phe | Gly 345 | Phe | Gly | Gly | Glu | Arg 350 | Met | Gly |
| Ile | Val | Asn 355 | Gly | Asp | Phe | Asn | Ala 360 | Thr | Ile | Ser | Leu | Lys 365 | Ser | Asp | Met |